(12) United States Patent
Davis et al.

(10) Patent No.: US 6,371,450 B1
(45) Date of Patent: Apr. 16, 2002

(54) BATTERY POWERED VOLATILE DISPENSER HAVING AN ELECTRICAL POWER CUT-OFF FOR A VISIBLE FAN

(75) Inventors: Brian T. Davis, Burlington, WI (US); John J. Gatzemeyer, Neshanic Station, NJ (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/347,590

(22) Filed: Jul. 1, 1999

(51) Int. Cl.[7] .................................................. B01F 3/04
(52) U.S. Cl. ......................... 261/26; 261/30; 261/104; 261/DIG. 88; 422/124
(58) Field of Search ........................... 261/26, 30, 104; 261/DIG. 65, DIG. 88; 422/124

(56) References Cited

U.S. PATENT DOCUMENTS

| | | |
|---|---|---|
| 3,990,848 A | 11/1976 | Corris |
| 4,035,451 A | 7/1977 | Tringali |
| 4,276,236 A | 6/1981 | Sullivan et al. |
| 4,301,095 A | 11/1981 | Mettler et al. |
| 4,377,399 A | 3/1983 | Bryson |
| 4,383,951 A * | 5/1983 | Palson ........................ 261/30 |
| 4,432,938 A | 2/1984 | Meetze, Jr. |
| 4,666,638 A | 5/1987 | Baker et al. |
| 4,743,406 A | 5/1988 | Steiner et al. |
| 4,830,791 A | 5/1989 | Muderlak et al. |
| 4,840,770 A | 6/1989 | Walz et al. |
| 4,857,240 A * | 8/1989 | Rearnes et al. ............... 261/26 |
| 4,931,224 A | 6/1990 | Holzner, Sr. |
| 5,038,972 A * | 8/1991 | Muderlak et al. .............. 222/25 |
| 5,133,042 A | 7/1992 | Pelonis |
| 5,147,582 A | 9/1992 | Holzner, Sr. et al. |
| 5,175,791 A | 12/1992 | Muderlak et al. |
| 5,259,062 A | 11/1993 | Pelonis |
| 5,282,334 A | 2/1994 | Kimura et al. |
| 5,342,584 A * | 8/1994 | Fritz et al. ................... 422/124 |
| 5,370,829 A | 12/1994 | Kunze |
| 5,376,338 A | 12/1994 | Zlotnik |
| 5,431,885 A | 7/1995 | Zlotnik |
| 5,547,616 A | 8/1996 | Dancs et al. |

FOREIGN PATENT DOCUMENTS

| | | |
|---|---|---|
| EP | 0 485 134 A | 4/1991 |
| EP | 0 485 134 A2 | 4/1991 |
| EP | 775 441 A1 | 8/1995 |

OTHER PUBLICATIONS

Patent Abstract of Japan /Publication No. 04024029/Matsushita Electric Ind Co Ltd.

Patent Abstract of Japan/Publication No. 04371160/Matsushita electric Works Ltd.

* cited by examiner

*Primary Examiner*—Robert A. Hopkins

(57) ABSTRACT

A battery powered volatile dispenser for dispensing a volatile material, the volatile dispenser including a housing having an air inlet, an air outlet, an airflow path therebetween, and a holder for a volatile reservoir for supplying a volatile to be introduced into air flowing in the airflow path. The volatile dispenser has a fan adapted to be powered by a battery, the fan being so located that it propels air through the airflow path and also is unrestrictedly visible to a user of the volatile dispenser. The volatile dispenser also has an electrical power cut-off that activates to cut off power to the fan when the battery voltage drops beneath a selected level greater than zero to provide a prominent visual cue of battery depletion. A method of providing a prominent visual cue of battery or volatile depletion by use of the volatile dispenser is also disclosed.

22 Claims, 3 Drawing Sheets

BATTERY POWERED VOLATILE DISPENSER HAVING AN ELECTRICAL POWER CUT-OFF FOR A VISIBLE FAN

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to battery powered, fan-driven volatile dispensers.

The art has produced a variety of fan-driven devices for dispensing volatile materials into the air. Typically such devices include a housing, an air inlet and outlet with an airflow path extending therebetween, a fan to produce an airflow in the airflow path, and a variety of means for introducing the volatile materials into the airflow path. A number of these fan-driven devices utilize battery power to drive the fan.

Of particular relevance to the instant invention are such battery powered devices that utilize a replaceable cartridge or refill assembly for renewing the supply of volatile materials to be dispensed by the device. Dancs et al., U.S. Pat. No. 5,547,616 and Ito et al., European Patent Application, EP 0775441 are specific examples of such devices. The disclosures of these patents and all other publications referred to herein are incorporated herein by reference as if fully set forth.

An important problem for a user of a battery-powered, fan-driven, volatile dispensing device is detecting when either the battery or the volatile material is depleted. A low voltage battery may still turn a fan, for example, but only at a reduced rate so that an inadequate amount of the volatile ingredient is dispensed. Similarly, the volatile supply may be used up before the battery is depleted, with the same result of inadequate amounts of volatile being dispensed. If the volatile ingredient is an air scent, a user might be able to detect inadequate dispensing simply by noticing a reduced amount of scent in the air. However, it can be difficult to notice a lowered level of a volatile when the volatile is an essentially odorless insect control agent.

Muderlak et al., U.S. Pat. No. 5,175,791 uses a timer circuit to step up power over time to the heater utilized to cause the active ingredient to be dispensed. The Muderlak et al. '791 device is not battery driven, does not utilize a fan, and is noted only for its general use of a timer circuit to adjust dispenser function in response to anticipated volatile depletion. Kunze, U.S. Pat. No. 5,370,829, discloses timed operation of a battery-driven fan. However, the timer appears not to be designed to measure or respond to consumption of either battery power or volatile ingredient.

Walz et al., U.S. Pat. No. 4,840,770, does not include a timer or indicator device but does utilize an amount of a gel-like odor control product selected to be sufficient that battery life and the life of the volatile ingredient are about the same. As a consequence, the "product and battery can be installed and replaced at the same time as a unit, thus assuring that an old battery is not left in by mistake." (Column 7 at Lines 49–52). However, Walz et al. does not teach any effective use-up cue or other response to a partially depleted battery that is may still be capable of turning a fan but only at an inadequately slow rate.

Sullivan et al., U.S. Pat. No. 4,276,236 and Tringali, U.S. Pat. No. 4,035,451, both disclose a cylindrical cartridge having a conventional, cylindrical battery held at the longitudinal axis of the cartridge, with a space between the battery and the outer wall of the cartridge holding a fluted strip of paper bearing active ingredient. The battery is integrally fastened within the cartridge. The Tringali and Sullivan cartridges permanently mount the battery within the same cartridge that carries the device's supply of volatile ingredient. Although no use-up indicator is supplied, at least the battery and volatile material must of necessity be replaced at the same time.

The Dancs et al device does directly address the issue of a battery depletion cue, relating it to volatile use-up. It uses conventional, replaceable batteries, such as D-cells, and a replaceable refill assembly bearing a finite quantity of volatile active ingredient to be dispensed. Volatile active ingredient is loaded on the refill assembly in an amount calculated to be depleted approximately upon the passage through the air flow path of that volume of air that the device's fan will deliver before an initially fresh battery is discharged below a selected level. Thus, depletion of the battery corresponds with active ingredient depletion and signals the need to replace both the battery and the refill assembly.

The Dancs et al device uses a control circuit to sense the condition of the battery, preferably by responding to voltage drop. The control circuit turns off the power to the fan when the battery condition reaches the level that should correspond to or just anticipate active ingredient depletion. The Dancs et al control circuit includes an LED or other small signal light that either is on or off to provide a visual cue to the user that the battery is being drained to a level approaching that at which power to the fan will be turned off. Consequently, a user of the dispensing device is given advance warning of device shut down.

The Dancs et al visible use-up cue can be effective but does present certain disadvantages. It requires a relatively expensive, specialty control circuit that must perform multiple tasks, sensing battery condition, actuating a light, and (eventually) cutting power to the fan. The light can be difficult to see in daylight or other well-illuminated conditions. Even when it is visible, the significance of the light's condition can be ambiguous, confusing a user. For example, does an illuminated red light signal that the device is running or that it is about to stop running? Multiple lights are possible—for example green to indicate that the device is operating and red to indicate an approaching motor turn-off. However, the necessary control circuits and lights add considerable cost to the device.

The art thus is aware of various control mechanisms in fan volatile dispensers, control mechanisms that provide use-up indicators or timing circuits to measure the use or indicate the depletion of either the battery or the volatile material being dispensed. However, such devices typically require lighting circuits for visual cues or provide no affirmative power cut-off prior to a fan's inadequate operation owing to low battery voltage.

Various other devices are believed to exist in the art, and those referred to, above, are by way of example only. A need still exists in battery-powered volatile dispensers for dispensing volatiles for an economical, simple, visually obvious cue for volatile supply use-up, combined with detection of and a visual cue for battery levels inadequate to run a fan at a speed or with a power sufficient to dispense a desired amount of volatile.

BRIEF SUMMARY OF THE INVENTION

The following definitions apply herein:

A fan is defined herein as being "unrestrictedly visible" if it is visible to a user viewing the volatile dispenser from the front when the volatile dispenser is in its normal position of use, without the presence of a visually obstructing grid or similar structure and without the need to remove any part of the volatile dispenser or any volatile reservoir used with the volatile dispenser. A grid or similar structure will be deemed "visually obstructing" if it prevents a viewer from observing more than 40, preferably not more than 30, and most preferably more 20 percent of the fan. Ideally, there is no grid or similar structure at all.

A "visual cue" is a visually detectable change in appearance that serves as a signal to the observer. A "prominent" visual cue in a device is a visual cue that is apparent to a user of the device upon even casual observation under the lighting and distances characteristic of typical daytime use or inspection conditions.

An "effective" level or "effective" amount is that level or amount sufficient to achieve the desired purpose.

A fan is operating at a "dispensing speed" if its speed is sufficient to create an air flow in an amount effective to dispense volatile from the volatile reservoir in the amount desired.

The invention provides a battery powered volatile dispenser for dispensing a volatile material. The volatile dispenser has a housing having an air inlet, an air outlet, an airflow path therebetween, together with a holder for a volatile reservoir for supplying a volatile to be introduced into air flowing in the airflow path. A fan is included that is adapted to be powered by a battery. The fan is so located that it propels air through the airflow path and also is unrestrictedly visible to a user of the volatile dispenser.

The volatile dispenser of the invention also has an electrical power cut-off that activates to cut off power to the fan when the battery voltage drops beneath a selected level greater than zero. Because the fan is unrestrictedly visible to a user of the volatile dispenser, cutting power to and thereby stopping the fan provides a prominent visual cue of battery depletion.

Preferably, the volatile dispenser is adapted for use with a replaceable volatile reservoir having a known quantity of volatile available for dispensing. The preferred volatile reservoir includes a substrate releasably bearing the volatile to be dispensed, preferably held in a frame or other structure that facilitates handling. The "refill assembly" and associated "substrate" disclosed in Dancs et al., U.S. Pat. No. 5,547,616, is suitable and is preferred. The battery voltage level beneath which the electrical power cut-off activates is the battery voltage level remaining after the fan has run sufficiently long to reduce the quantity of volatile in the reservoir to a selected level. Consequently, the cut-off of power, Which stops operation of the fan, provides a prominent visual cue for volatile depletion to the selected level. It is further preferred that the electrical power cut-off activates to cut off power to the fan at a battery voltage level still effective to power the fan at a dispensing speed.

In another preferred embodiment, the fan of the volatile dispenser is a propeller blade-type fan having a hub and radially extending blades, with the fan being sufficiently contained within a well to substantially prevent a user from touching the tips of the fan from a direction radial to the hub. Most conveniently, the well is formed as a part of the housing.

In yet another preferred embodiment, the housing of the volatile dispenser has a bottom surface and a door located in the bottom surface through which a battery may be inserted to power the fan. The housing is so formed that the door must be closed before the housing can be set in its position of use, with the weight of the volatile dispenser substantially resting on the door.

It is further preferred that the housing of the volatile dispenser have a bottom surface and that the volatile dispenser be taller than the smaller of the front-to-back and side-to-side dimensions of the bottom surface, so that the volatile dispenser presents an upright, relatively slender and tall appearance. The volatile dispenser further preferably includes a battery holder located within the housing and positioned to hold a battery adjacent to the bottom surface, effectively lowering the center of gravity of the volatile dispenser when a battery is in place in the holder. This arrangement increases the stability of the volatile dispenser when it is resting on its bottom surface. Preferably, the volatile dispenser includes a door located in the bottom surface of the housing through which a battery may be inserted into the battery holder, the housing being so formed that the door must be closed before the housing can be set in its position of use. Further, it is preferred that the door must be closed to retain a battery in the battery holder when the volatile dispenser is oriented in its position of function.

The method of the invention of signaling a user of a battery powered volatile dispenser for dispensing a volatile material from a reservoir of the material that the reservoir has been depleted to a selected degree is summarized as follows. As one step, the person performing the method must provide a reservoir of the volatile material, the reservoir having a known capacity and known volatile delivery characteristics.

As another step, the person performing the method must provide and install the reservoir in a battery powered volatile dispenser capable of dispensing volatile material from the reservoir and having (i) a fan adapted to be powered by a battery, the fan being so located that it propels air along an airflow path to pick up the volatile material from the reservoir, the fan being unrestrictedly visible to a user of the volatile dispenser; and (ii.) an electrical power cut-off that activates to cut off power to the fan when the battery voltage drops beneath a selected level greater than zero, the voltage level being calculated to be the battery voltage level remaining after the fan has run sufficiently long to reduce the quantity of volatile in the reservoir to the selected degree, so that the cut-off of power, which stops operation of the fan, provides a prominent visual cue for volatile depletion to the selected level.

The final step is to activate the volatile dispenser and observe the movement of the fan. A preferred added step is to select the battery voltage level at which the electrical power cut-off activates to be a voltage level still effective to power the fan at a dispensing speed.

DETAILED DESCRIPTION OF THE INVENTION

Figure 1:
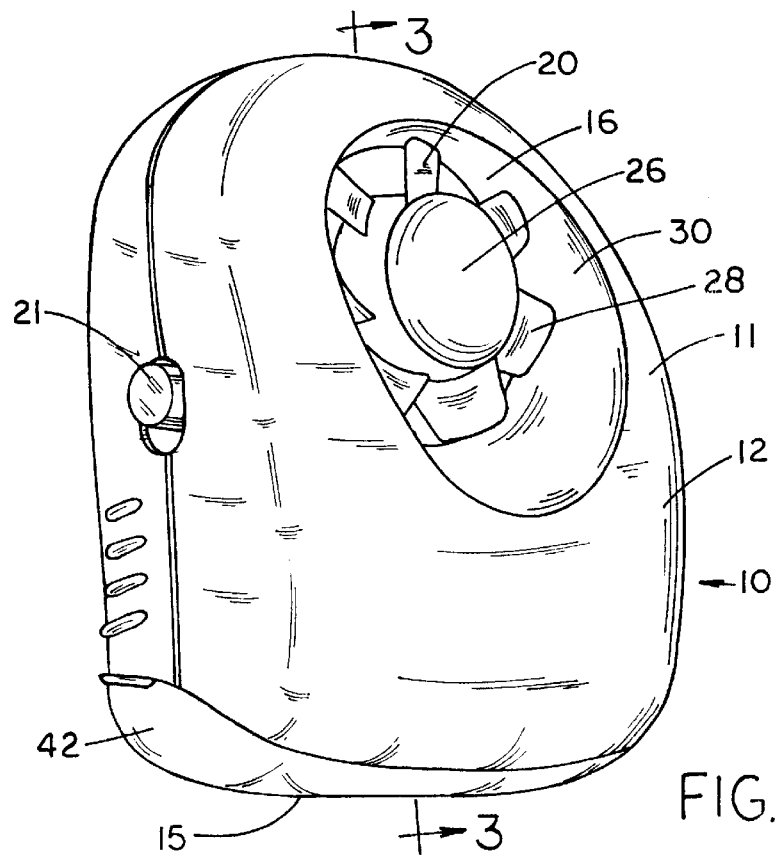
FIG. 1 is a perspective view from the front of a first embodiment of the battery powered volatile dispenser of the invention.
Figure 2:
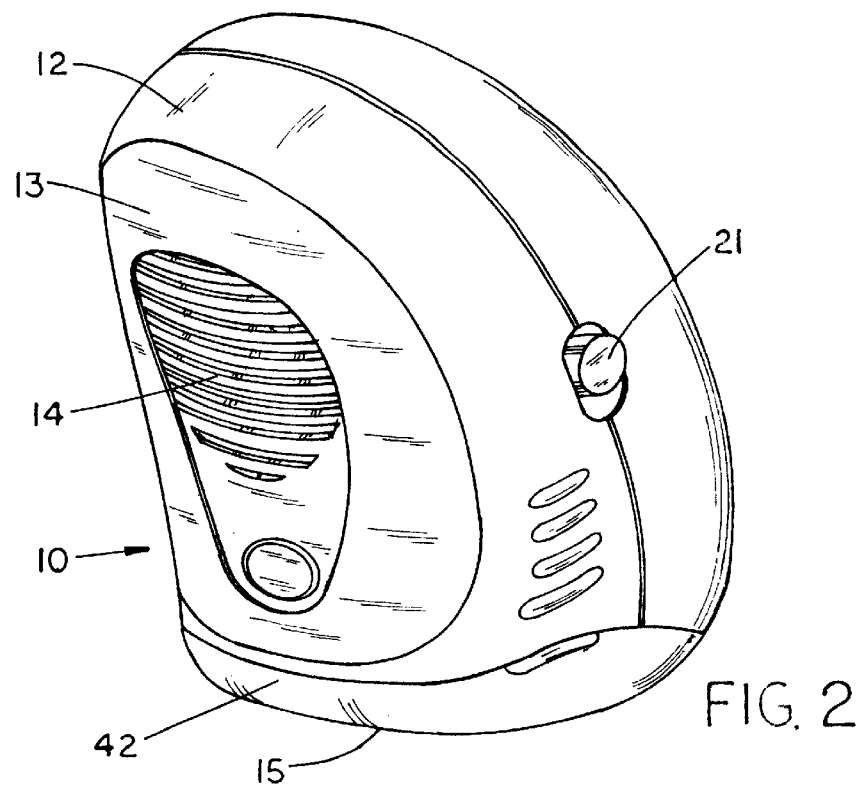
FIG. 2 is a perspective view from the back of the embodiment of FIG. 1.

Turning now to the drawings, wherein like reference numbers refer to like and corresponding parts throughout the several views, a first embodiment of the battery powered volatile dispenser of the invention is shown generally at 10 in FIGS. 1 and 2. The volatile dispenser 10 can be manufactured out any convenient plastic by conventional plastic forming methods. The volatile dispenser 10 has a housing 12 having a front surface 11, back surface 13 and foot 15.

The housing 12 also has an air inlet, an air outlet, and interior surfaces defining an air flow path therebetween. The volatile dispenser 10 is adapted to cause air to flow in through the inlet and out through the outlet by means discussed below. Preferably the air inlet is located in the back surface 13 and the air outlet is located in the front surface 11, as is shown at 14 and 16, respectively, in FIGS. 1–3. The air flow path is shown at 18 in FIG. 3, and, in the preferred arrangement, air moves through the volatile dispenser 10 along the air flow path from back to front, as is indicated by the arrows in FIG. 3. However, the opposite air flow direction is also possible, as will be discussed below.

Figure 3:
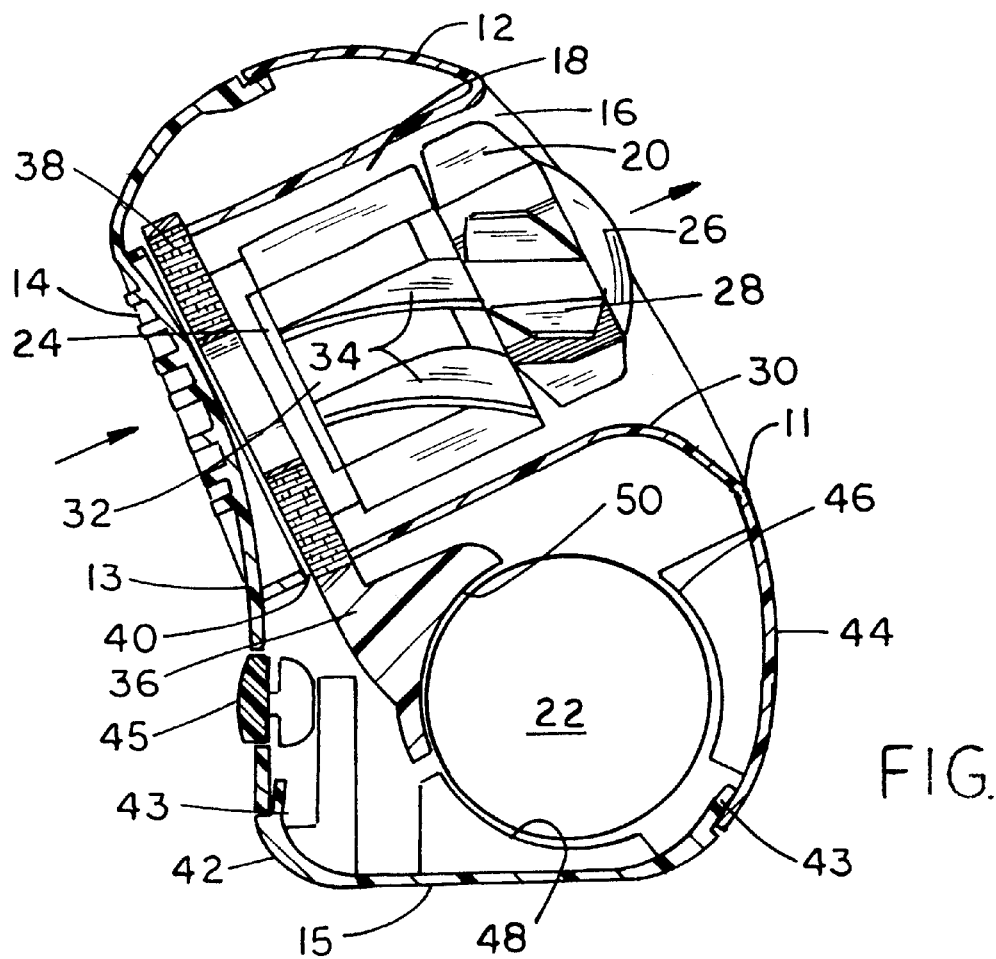
FIG. 3 is a cross sectional view of the embodiment of FIG. 1, taken along section lines 3—3 of FIG. 1.

The volatile dispenser 10 includes a fan 20 adapted to be powered by a battery, shown schematically in FIG. 3 at 22. The fan 20 propels air through the airflow path 18, preferably being located directly in the airflow path, as illustrated in the Figures. The fan 20 is unrestrictedly visible to a user of the volatile dispenser 10, preferably by observation from the front of the volatile dispenser. The term "unrestrictedly visible" is used here with the meaning given above.

Battery 22 is electrically connected with the fan 20 by wires or other conventional means (not shown). Preferably, a switch such as that shown at 21 in FIGS. 1–2 is provided to allow a user to turn the fan 20 on and off. The volatile dispenser 10 includes a conventional electrical power cut-off selected to activate to cut off power to the fan when the battery voltage drops beneath a selected level greater than zero. The power cut-off is shown schematically in FIG. 3 at 24. When the power cut-off 24 activates to cut off power to the fan 20, the fan immediately stops turning, which can be directly observed by a user of the volatile dispenser, thus providing a prominent visual cue of battery depletion. The terms "visual cue" and "prominent" are used with the meanings given above.

Although any suitable type of fan is within the scope and breadth of the invention if it can be so installed as to be unrestrictedly visible to a user when it is in operation, preferably the fan 20 is a propeller blade-type fan, as is shown in FIGS. 1 and 3, having a central hub 26 and radially extending blades 28. Preferably, the housing 12 has surfaces that define a well in either the front or back surface (11,13) but preferably in the front surface 11, as is shown at 30 in FIGS. 1 and 3. The fan 20 is located within the well 30 and is sufficiently contained therein to substantially prevent a user from touching the tips of the fan blades 28 from a direction radial to the hub 26.

Preferably the fan 20 is driven by a conventional in-line electric motor, such as that shown schematically in half round at 32 in FIG. 3, and the in-line motor is supported by static vanes that extend from the motor to the interior surfaces that define the airflow path 18, as is shown at 34 in FIG. 3. When it is desired to project a more columnar air flow from the air outlet 16 than would otherwise be the case, it is preferred that the static vanes 34 be formed with a circumferential twist opposite in direction from that in which the fan 20 turns such that air flowing through the air flow path 18 is swirling circumferentially when it reaches the fan in a direction opposite to that in which the fan is turning.

The volatile dispenser 10 is adapted for use with a replaceable volatile reservoir having a known quantity of volatile available for dispensing. Any volatile reservoir can be used if it is capable of providing a surface within the air flow path 18 from which the volatile material to be dispensed may be evaporated by air flowing within the air flow path. By way of example only, this includes volatile reservoirs holding a volatile liquid that is carried to the air flow path via a wick; reservoirs exposing to the air flow path volatile-emitting gels or liquids held in cups or by other structures with or without intervening membranes or screens; polymers, ceramics, papers, or other solids impregnated or coated with volatile materials for exposure to the air flow path, and the like.

Figure 4:
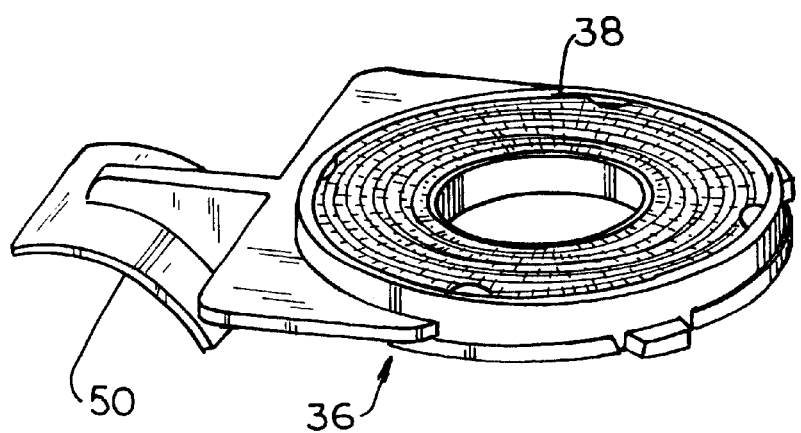
FIG. 4 is a perspective view from above and to the front of a refill insert suitable for use with the battery powered volatile dispenser of the invention.

However, the preferred volatile reservoir is a refill insert of the sort identified and described in Dancs et al., U.S. Pat. No. 5,547,616 as "refill assembly 28." The refill insert shown generally at 36 in FIG. 4 is most preferred, being of the design shown in Gatzemeyer et al., U.S. Pat. No. Des. 392,733. Thus the preferred refill insert 36 is as described in Dancs et al., with an air-transmitting substrate 38 that is treated with the volatile to be dispensed. Preferably, the substrate 38 is planar and is of a shape and size approximately the same as the cross-sectional shape and size of the airflow path 18. Preferably, the substrate is made of coiled corrugated cardboard, with the corrugation channels oriented generally parallel to the flow of air in the air flow path, when the refill insert 36 is in position within the air flow path. However, open meshes, other reticulated papers or plastics, and the like are also within the scope and spirit of the invention. The central hole shown in the substrate 38 of FIG. 4 is an optional but not necessary feature that is possible because a majority of the air moving through the airflow path 18 is at its periphery when a propeller-type fan is used. Thus, omitting the center of the substrate 38 can improve manufacturing economy without importantly reducing volatile exposure to moving air in the air flow path 18.

The interior surfaces that define the airflow path 18 of the volatile dispenser 10 include a slot 40 into which the substrate 38 of the refill insert 36 may be inserted to position the substrate in the air flow moving through the airflow path. Preferably interior surfaces of the volatile dispenser 10 receive and so interact with surfaces of the refill insert 36 as to conveniently guide the refill insert into its correct position within the volatile dispenser. Preferably, guiding structures both of the refill insert 36 and the interior of the volatile dispenser 10 are provided and generally correspond to those disclosed in Dancs et al. They are not separately shown or discussed herein.

The housing 12 includes a door 42. The remainder of the housing 12 other than the door 42 will be referred to as the "main housing 44." The door 42 preferably is entirely removable and is held in place, when closed, by conventional interlocking edges 43 and a depressible snap button 45, as seen in FIG. 3. The size and location of the door 42, preferably in the bottom surface or foot 15 of the housing 12 is such that the volatile dispenser 10 cannot be placed in its position of function until the door is closed. The volatile dispenser 10 also includes a battery holder 46 extending from the main housing 44, and a battery, such as battery 22, can be inserted through the opening made by opening the door 42 to rest against surfaces of the battery holder that are adapted to receive and engage a selected portion of the a surface of the battery, preferably a portion of the arc defined by the sides of a cylindrical battery, such as a conventional D-cell. The battery holder 46 engages the battery 22 in a manner such that, while the location of an installed battery is determined by the battery holder, an installed battery will fall out of its installed position if the volatile dispenser 10 is placed in its normal position of function without further restriction of battery movement. Preferably, the battery holder 46 contacts only upper or side portions of an installed battery 22, an arrangement shown in FIG. 3.

The door 42 also has battery contact surfaces 48, visible in FIG. 3, that further define the installed position of the battery 22, when the door is closed, the battery contact surfaces 48 and the battery holder 46 coacting to secure an installed battery in place, but only when the door 42 is closed.

The refill insert 36 preferably has brace surfaces 50 that present toward and contact a properly installed battery 22, preferably engaging the curved side of a conventional cylindrical battery. The battery holder 46 holds the battery 22 in such a manner that a refill insert 36 not fully inserted in place in the air flow path 18 blocks placement of a battery in the battery holder, providing a signal to a user that the position of the refill insert needs to be corrected. However, when the refill insert 36 is correctly inserted and the battery 22 is in place, the brace surfaces 50 engage the battery, both stabilizing the battery in the battery holder and ensuring that the refill insert remains in the correct position for use. By this means, successful placement of a battery 22 in the battery holder 46 serves to both verify and maintain the correct placement of the refill insert 36 in the airflow path 18. Furthermore, the arrangement disclosed above with respect to the battery contact surfaces 48 of the door 42 additionally requires that the door be closed, completing the housing 12, before the volatile dispenser 10 will be operative.

Although a cylindrical battery is shown in the drawings, with convenient, curved brace surfaces 50 and battery holder and battery contact surfaces 46,48, the same basic arrangement may be accomplished with batteries and brace surfaces of other shapes. Such alternative arrangements are within the breadth and scope of the invention.

The preferred shape and operating posture of the volatile dispenser 10 is that of a slender, upright structure, with the foot 15 of the housing 12 being of a smaller area than either the front or back surfaces 11,13. Among other aesthetic and functional advantages, this arrangement tends to present the fan 20 toward a user standing generally in front of the volatile dispenser 10, increasing the likelihood that the user will observe the movement or lack of movement of the fan. Unfortunately, this shape and posture also increases the likelihood of tip-over of the volatile dispenser 10. However, with the preferred battery arrangement just disclosed, the battery 22 is located adjacent to the door 42, essentially at the level of the foot 15 of the housing 12. Typically, the battery is the heaviest element of a device such as the volatile dispenser 10, when the housing is made of plastic and the motor 32 is a typical, small, low-voltage motor. The result is that the volatile dispenser 10 has a low overall center of gravity when a battery 22 is in place in the battery holder 46, and the likelihood of tip-over is reduced.

Alternatively expressed, the housing 12 has a bottom surface and is taller than the smaller of the front-to-back and side-to-side dimensions of the bottom surface. The battery holder 46 is located within the housing 12 and is positioned to hold a battery 22 adjacent to the bottom surface, effectively lowering the center of gravity of the volatile dispenser 10, when a battery is in place in the holder. The result is to increase the stability of the volatile dispenser 10 when it is resting on its bottom surface.

Preferably the refill insert 36 is loaded with the volatile to be dispensed in an amount selected to be such that the quantity of volatile in the reservoir will be reduced to a selected level shortly before the battery is so depleted that it can no longer drive the fan at a "dispensing speed," as that term has been defined, above. The electrical power cut-off 24 is then selected to be such that the battery voltage level beneath which the power cut-off activates is the battery voltage level remaining after the fan 20 has run sufficiently long to reduce the quantity of volatile in the reservoir to the selected level. Thus, the cut-off of power, which stops operation of the fan 20, provides a prominent visual cue for volatile depletion to the selected level. The terms "prominent" and "visual cue" in this context are defined, above.

Figure 5:
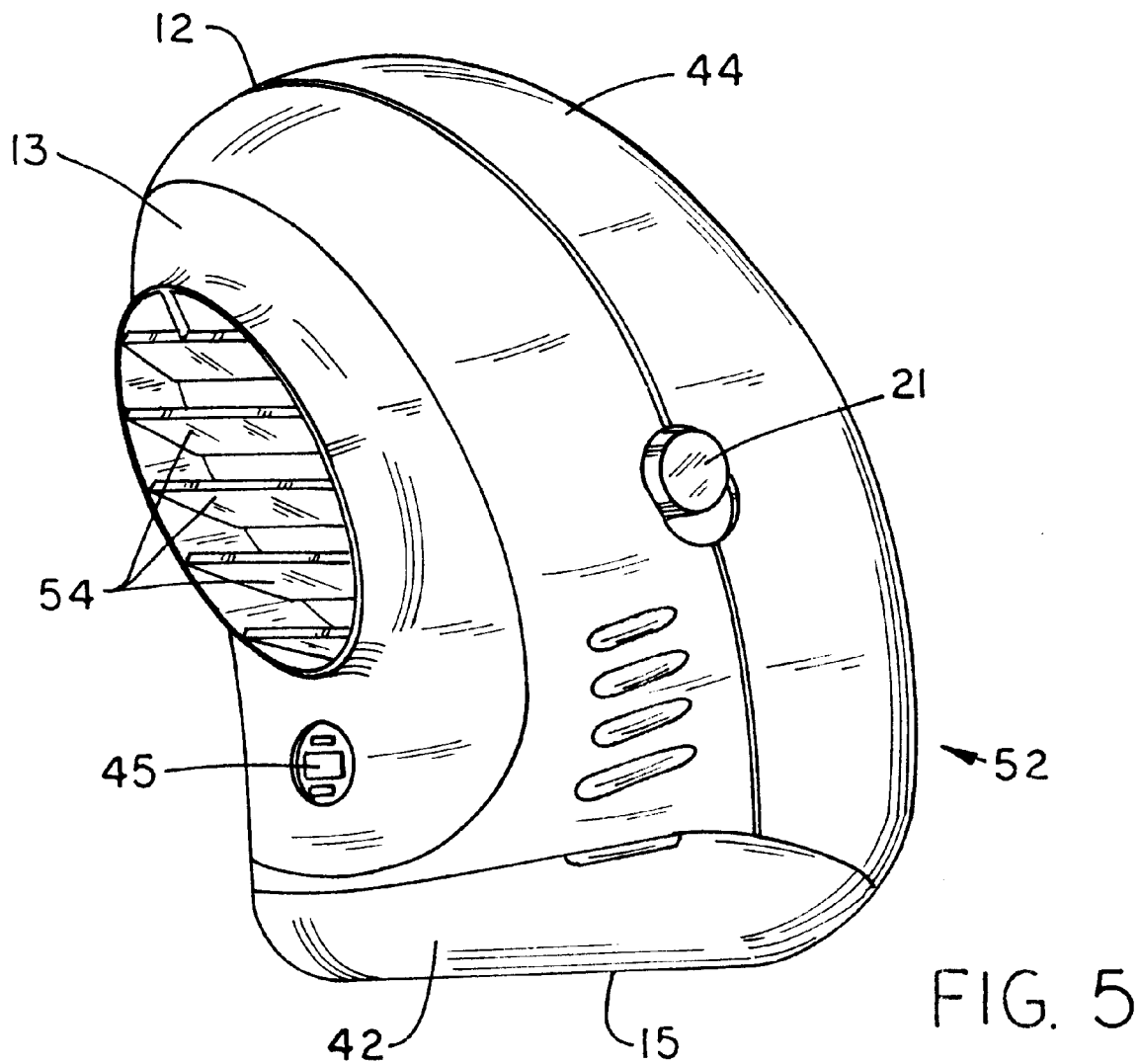
FIG. 5 is a perspective view from the back of a second embodiment of the battery powered volatile dispenser of the invention.

The preferred direction of airflow through the air flow path 18 is from back to front, but, as has been noted, the opposite airflow direction is also possible and is within the scope and spirit of the invention. Although no changes in the volatile dispenser 10 are required for a front to back air flow direction, except to reverse the motor direction, the pitch of the blades of the fan 20, or some similar step to correctly drive the airflow, the embodiment of the volatile dispenser of the invention shown generally at 52 in FIG. 5 includes advantageous adaptations for the purpose. All features that are the same as those of the embodiment 10 of the previous Figures have been given the same references numbers and will not be separately discussed.

When a front to back airflow direction is employed, the air outlet is in the back surface 13 of the housing 12, of course. Because many times the stream of air thus exiting at the back of the volatile dispenser 52 may be flowing toward a wall or the like, directional vanes 54 at the back end of the air flow path are preferred to direct exiting air upwardly and thus to improve its mixing with the remainder of the air in a room. Furthermore, the twisted static vanes 34 of embodiment 10, while still possible, are no longer important to forming a projected air exhaust. The corresponding structure (not shown) of volatile dispenser 52 can be straight.

The method of signaling a user of a battery powered volatile dispenser for dispensing a volatile material from a reservoir of the material that the reservoir has been depleted to a selected degree includes the following steps. One must provide a reservoir of the volatile material to be dispensed, the reservoir having a known capacity and known volatile delivery characteristics. One also must provide a battery powered volatile dispenser capable of dispensing volatile material from the reservoir and must installing the reservoir in the dispenser. The dispenser must have a fan adapted to be powered by a battery, the fan being so located that it propels air along an airflow path to pick up the volatile material from the installed reservoir, the fan being unrestrictedly visible to a user of the volatile dispenser. The dispenser must also have an electrical power cut-off that activates to cut off power to the fan when the battery voltage drops beneath a selected level greater than zero. The voltage level must be calculated to be the battery voltage level remaining after the fan has run sufficiently long to reduce the quantity of volatile in the reservoir to the selected degree, so that the cut-off of power, which stops operation of the fan, provides a prominent visual cue for volatile depletion to the selected level. The user must then activate the volatile dispenser and observe the movement of the fan. Preferably, the method also includes the step of selecting the battery voltage level at which the electrical power cut-off activates to be a voltage level still effective to power the fan at a dispensing speed.

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

INDUSTRIAL APPLICABILITY

A device and method are described for an economical and practical visual use-up cue in battery-powered, volatile dispensers for dispensing a volatile material, coupled with a means for preventing operation of such a device at an inadequate battery power level. Such devices are of practical application in room scenting, insect control, and the like.

What is claimed is:

1. A battery powered volatile dispenser for dispensing a volatile material, the volatile dispenser comprising:
   a. a housing having an air inlet, an air outlet, an airflow path therebetween, and a holder for a volatile reservoir for supplying a volatile to be introduced into air flowing in the airflow path;
   b. a fan adapted to be powered by a battery, power being supplied from the battery to the fan through a switch, the switch having an on position and an off position, the on position allowing power to the fan and the off position cutting off power to the fan, the fan being so located that it propels air through the airflow path and also is unrestrictedly visible to a user of the volatile dispenser; and
   c. an electrical power cut-off that activates to cut off power to the fan when the battery voltage drops beneath a selected level greater than zero to provide a prominent visual cue of battery depletion,
      wherein the volatile dispenser is for use with a replaceable volatile reservoir having a known quantity of volatile available for dispensing, wherein the battery voltage level beneath which the electrical power cut-off activates is the battery voltage level remaining after the fan has run sufficiently long to reduce the quantity of volatile in the reservoir to a selected level, so that the cut-off power, which stops operation of the fan, provides the prominent visual cue for volatile depletion to the selected level, wherein the visual cue is the stopped fan, and wherein the switch and the electrical power cut-off are the only mechanisms to cut off power to the fan such that a user knows that fan stoppage only corresponds to the switch being in the off position or the reduction of the quantity of volatile in the reservoir to the selected level.

2. The volatile dispenser of claim 1 wherein the electrical power cut-off activates to cut off power to the fan at a battery voltage level still effective to power the fan at a dispensing speed.

3. The volatile dispenser of claim 1 wherein the fan is a propeller blade-type fan having a hub and radially extending blades, and the fan is sufficiently contained within a well to substantially prevent a user from touching the tips of the fan from a direction radial to the hub.

4. The volatile dispenser of claim 1 wherein the housing has a bottom surface and a door located in the bottom surface through which a battery may be inserted to power the fan, the housing being so formed that the door must be closed before the housing can be set in its position of use, with the weight of the volatile dispenser substantially resting on the door.

5. The volatile dispenser of claim 1 wherein the housing has a bottom surface and is taller than the smaller of the front-to-back and side-to-side dimensions of the bottom surface, the volatile dispenser further including a battery holder located within the housing and positioned to hold a battery adjacent to the bottom surface, effectively lowering the center of gravity of the volatile dispenser, when a battery is in place in the holder, increasing the stability of the volatile dispenser when it is resting on its bottom surface.

6. The volatile dispenser of claim 5 wherein a door is located in the bottom surface of the housing through which a battery may be inserted into the battery holder, the housing being so formed that the door must be closed before the housing can be set in its position of use.

7. The volatile dispenser of claim 6 wherein the door must be closed to retain a battery in the battery holder when the volatile dispenser is oriented in its position of function.

8. A method of signaling a user of a battery powered volatile dispenser for dispensing a volatile material from a reservoir of the material that the reservoir has been depleted to a selected degree, comprising the steps of
   a. providing a reservoir of the volatile material, the reservoir having a known capacity and known volatile delivery characteristics;
   b. providing and installing the reservoir in a battery powered volatile dispenser capable of dispensing volatile material from the reservoir and having
      i. a fan adapted to be powered by a battery, power being supplied from the battery to the fan through a switch, the switch having an on position and an off position, the on position allowing power to the fan and the off position cutting off power to the fan, the fan being so located that it propels air along an airflow path to pick up the volatile material from the reservoir, the fan being unrestrictedly visible to a user of the volatile dispenser; and
      ii. an electrical power cut-off that activates to cut off power to the fan when the battery voltage drops beneath a selected level greater than zero, the voltage level being calculated to be the battery voltage level remaining after the fan has run sufficiently long to reduce the quantity of volatile in the reservoir to the selected degree, so that the cut-off of power, which stops operation of the fan, provides a prominent visual cue for volatile depletion to the selected level, the visual cue being the stopped fan, wherein the switch and the electrical power cut-off are the only mechanisms to cut off power to the fan such that a user knows that fan stoppage only corresponds to the switch being in the off position or the reduction of the quantity of volatile in the reservoir to the selected level; and
   c. activating the volatile dispenser by way of the switch and observing the movement of the fan.

9. The method of claim 8 including the step of selecting the battery voltage level at which the electrical power cut-off activates to be a voltage level still effective to power the fan at a dispensing speed.

10. A battery powered volatile dispenser for dispensing a volatile material, the volatile dispenser comprising:
   a. a housing having an air inlet, an air outlet, an airflow path therebetween, and a holder for a volatile reservoir for supplying a volatile to be introduced into air flowing in the airflow path;

b. a fan adapted to be powered by a battery, the fan being so located that it propels air through the airflow path and also is unrestrictedly visible to a user of the volatile dispenser; and c. an electrical power cut-off that activates to cut off power to the fan when the battery voltage drops beneath a selected level greater than zero to provide a prominent visual cue of battery depletion, wherein the housing has a bottom surface and a door located in the bottom surface through which a battery may be inserted to power the fan, the housing being so formed that the door must be closed before the housing can be set in its position of use, with the weight of the volatile dispenser substantially resting on the door.

11. The volatile dispenser of claim 10 for use with a replaceable volatile reservoir having a known quantity of volatile available for dispensing, wherein the battery voltage level beneath which the electrical power cut-off activates is the battery voltage level remaining after the fan has run sufficiently long to reduce the quantity of volatile in the reservoir to a selected level, so that the cut-off power, which stops operation of the fan, provides a prominent visual cue for volatile depletion to the selected level.

12. The volatile dispenser of claim 11 wherein the electrical power cut-off activates to cut off power to the fan at a battery voltage level still effective to power the fan at a dispensing speed.

13. The volatile dispenser of claim 10 wherein the fan is a propeller blade-type fan having a hub and radially extending blades, and the fan is sufficiently contained within a well to substantially prevent a user from touching the tips of the fan from a direction radial to the hub.

14. The volatile dispenser of claim 10 wherein the housing has a bottom surface and is taller than the smaller of the front-to-back and side-to-side dimensions of the bottom surface, the volatile dispenser further including a battery holder located within the housing and positioned to hold a battery adjacent to the bottom surface, effectively lowering the center of gravity of the volatile dispenser, when a battery is in place in the holder, increasing the stability of the volatile dispenser when it is resting on its bottom surface.

15. The volatile dispenser of claim 14 wherein the door must be closed to retain a battery in the battery holder when the volatile dispenser is oriented in its position of function.

16. A battery powered volatile dispenser for dispensing a volatile material, the volatile dispenser comprising:

a. a housing having an air inlet, an air outlet, an airflow path therebetween, and a holder for a volatile reservoir for supplying a volatile to be introduced into air flowing in the airflow path;

b. a fan adapted to be powered by a battery, the fan being so located that it propels air through the airflow path and also is unrestrictedly visible to a user of the volatile dispenser; and c. an electrical power cut-off that activates to cut off power to the fan when the battery voltage drops beneath a selected level greater than zero to provide a prominent visual cue of battery depletion, wherein the housing has a bottom surface and is taller than the smaller of the front-to-back and side-to-side dimensions of the bottom surface, the volatile dispenser further including a battery holder located within the housing and positioned to hold a battery adjacent to the bottom surface, effectively lowering the center of gravity of the volatile dispenser, when a battery is in place in the holder, increasing the stability of the volatile dispenser when it is resting on its bottom surface.

17. The volatile dispenser of claim 16 for use with a replaceable volatile reservoir having a known quantity of volatile available for dispensing, wherein the battery voltage level beneath which the electrical power cut-off activates is the battery voltage level remaining after the fan has run sufficiently long to reduce the quantity of volatile in the reservoir to a selected level, so that the power cut-off, which stops operation of the fan, provides a prominent visual cue for volatile depletion to the selected level.

18. The volatile dispenser of claim 17 wherein the electrical power cut-off activates to cut off power to the fan at a battery voltage level still effective to power the fan at a dispensing speed.

19. The volatile dispenser of claim 16 wherein the fan is a propeller blade-type fan having a hub and radially extending blades, and the fan is sufficiently contained within a well to substantially prevent a user from touching the tips of the fan from a direction radial to the hub.

20. The volatile dispenser of claim 16 wherein the housing has a bottom surface and a door located in the bottom surface through which a battery may be inserted to power the fan, the housing being so formed that the door must be closed before the housing can be set in its position of use, with the weight of the volatile dispenser substantially resting on the door.

21. The volatile dispenser of claim 16 wherein a door is located in the bottom surface of the housing through which a battery may be inserted into the battery holder, the housing being so formed that the door must be closed before the housing can be set in its position of use.

22. The volatile dispenser of claim 21 wherein the door must be closed to retain a battery in the battery holder when the volatile dispenser is oriented in its position of function.

* * * * *